United States Patent [19]

Bisso et al.

[11] Patent Number: 4,920,049
[45] Date of Patent: Apr. 24, 1990

[54] PROCESS FOR THE CONTINUOUS PRODUCTION OF FRUCTOSE-1,6-DI-PHOSPHATE BY EMPLOY OF IMMOBILIZED YEAST

[75] Inventors: Guglielmo M. Bisso, Federico Melelli, both of Rome, Italy

[73] Assignee: Biomedica Foscama Industria-Chimico-Farmaceutica S.p.A., Rome, Italy

[21] Appl. No.: 73,451

[22] Filed: Jul. 15, 1987

[30] Foreign Application Priority Data

Aug. 6, 1986 [IT] Italy .................. 21422 A/86

[51] Int. Cl.$^5$ .................. C12P 19/02; C12N 11/04
[52] U.S. Cl. .................................. 435/105; 435/182
[58] Field of Search .............. 435/184, 174, 182, 287, 435/288, 290, 311, 105, 940, 941, 942, 105

[56] References Cited

U.S. PATENT DOCUMENTS

| 4,355,103 | 10/1982 | Boguslawski et al. | 435/94 |
| 4,599,311 | 7/1986 | Kawasaki | 435/68 |
| 4,666,852 | 5/1987 | Cork | 435/140 |
| 4,683,198 | 7/1987 | Ishikawa et al. | 435/882 |
| 4,767,707 | 8/1988 | Levesque et al. | 435/176 |

Primary Examiner—Barry S. Richman
Assistant Examiner—T. J. Wallen
Attorney, Agent, or Firm—Ladas & Parry

[57] ABSTRACT

The process provides the enzymatic phosphorylation of glucose to FDP by means of yeast immobilized by glutaraldehyde and the separation of FDP by ultrafiltration. A suspension of glutaraldehyde-treated yeast is fed to a fermenter, with addition of a nutrient mixture consisting of dextrose (1M), sodium phosphate (0.5 M), magnesium chloride (10 mM) and phosphoric acid until pH 6.5. The mixture is re-circulated through a hollow fiber ultrafiltration unit to separate the FDP that forms during the phosphorylation reaction.

7 Claims, 1 Drawing Sheet

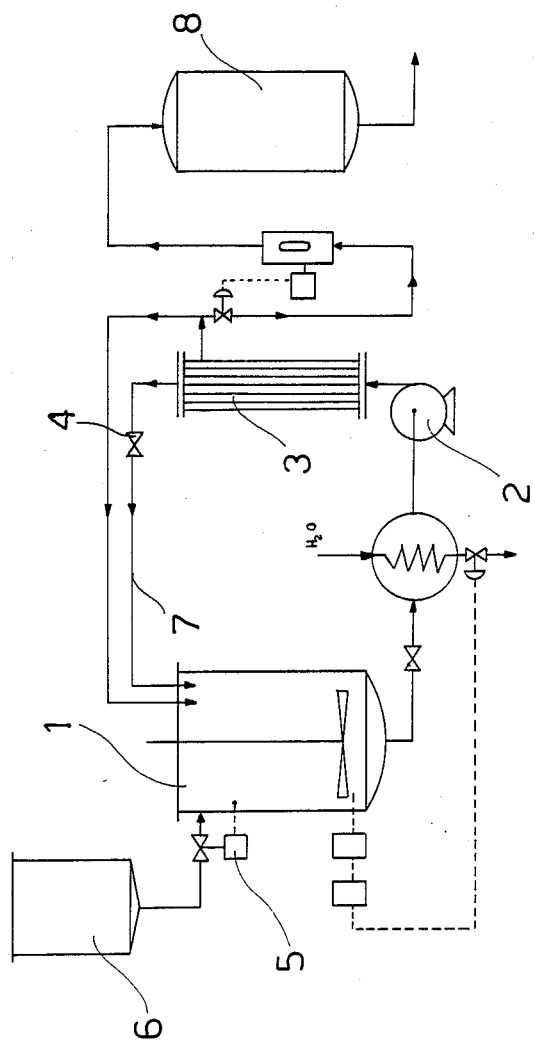

PROCESS FOR THE CONTINUOUS PRODUCTION OF FRUCTOSE-1,6-DI-PHOSPHATE BY EMPLOY OF IMMOBILIZED YEAST

The present invention provides a process for the continuous production of fructose-1,6-disphosphate and, more specifically, a process that combines the employ of the hollow fiber ultrafiltration with the enzymatic phosphorylation of glucose to FDP, carried out in a fermenter by means of yeast cells immobilized by glutaraldehyde.

The invention relates too to the plant for putting said process into effect.

The employ of fructose-1,6-disphosphate (FDP) and the salts thereof has been gaining ground recently, particularly in the pharmaceutical field; there has been accordingly an increase also in the industrial scale production of such a compound.

According to the prior art technique, FDP is obtained by phosphorylating glucose by means of yeast, whereby the phosphorylating properties of the latter are exploited.

In the course of this process, yeast exhausts itself because of the enzymatic losses connected with the outflow of FDP through the cell membranes; this makes it necessary to replace yeast at the completion of each phosphorylation cycle, which made continuous manufacture processes impossible to realize up to the present time.

The Applicant has recently put into practice a process-subject manner of the Italian patent Application No. 19865 A/86—that allows to preserve the phosphorylating activity of yeast, by means of the intracellular immobilization of the glycolytic enzymes by glutaraldehyde.

This process allows to "adjust" the cell permeability, whereby FDP is allowed to outflow from the inside of the cell, whilst the enzymatic losses that usually occur in the permeabilized yeast employed to this end are at the same time inhibited.

Thanks to the possibility of maintaining the properties of yeast almost unchanged, it has been possible to develop a process—subject of the present invention—for the continuous production of FDP.

More specifically, the process according to the invention provides the enzymatic phosphorylation of glucose to FDP, from yeast immobilized by glutaraldehyde, and the subsequent recovery of fructose-1,6-diphosphate in a hollow fiber ultrafiltration unit.

BRIEF DESCRIPTION OF THE DRAWING

The present invention will now be described in detail, with reference to the only attached drawing, that shows the diagram of a plant for the manufacture of FDP according to the invention process.

DETAILED DESCRIPTION OF THE DRAWING

The plant comprises substantially a fermenter 1 provided with stirrer and with means for keeping the temperature constant, and linked, via a peristaltic pump 2, to a hollow fiber ultrafiltration unit 3.

Between fermenter 1 and unit 3 is inserted a valve 4 of known type, allowing to adjust the speed of the liquid directed towards the ultrafiltration unit.

Fermenter 1 is further linked, through a second peristaltic pump 5, to a feed tank 6 containing a nutrient mixture of glucose and phosphates.

A conduit 7 joins the outlet of ultrafiltration unit 3 to fermenter 1, in order to allow yeast to be re-circulated, whilst a receiver 8 is linked to the hollow fiber unit 3, to collect the obtained FDP.

The process is carried out by preparing first a sufficient amount of permeabilized yeast (e.g. *Saccharomyces carlsbergensis*) treated with glutaraldehyde as described in the Italian patent Application No. 19865 A/86, to preserve its phosphorylating capability. The process according to the Italian patent, is carried out by adding a nutrient mixture (2M dextrose, 1M sodium phosphate and phosphoric acid unit pH 6.5.) to a suspension of 60% w/v yeast in tap water, and by heating for one hour to 35° C. under slow stirring. A 1–5% amount of a plasmolytic agent is added to the yeast suspension before the addition of the nutrient mixture. The glutaraldehyde is added to a suspension of permeabilized yeast cells and to which is added 10% disintegrated yeast at a final concentration of 0.25–1% w/v, at 28° C., under constant and slow stirring.

The yeast, thus treated, is suspended in water (30% weight/volume) and fed to fermenter 1; then an amount of nutrient mixture equal to half its volume is added, consisting of dextrose (1M), sodium phosphate (0.5M), magnesium chloride (10 mM) and phosphoric acid until pH 6.5.

The fermenter temperature is brought to 28° C. and, after setting valve 4 to the maximum aperture position, yeast is re-circulated through the ultrafiltration unit—from which it returns each time to the fermenter—for about 4 hours, a time necessary for the reaction to start.

During this stage, the pressure gradient throughout the fibers of the ultrafiltration unit being equal to zero, there is actually no permeation.

At the end of such first cycle, after a constant level of phosphorylation has been achieved, valve 4 is set to such an aperture position as to allow the complete change of the nutrient mixture over about 10 hours. During this step there is collected, through the fibers of unit 3, the FDP-containing permeated substance that is stored in receiver 8, while yeast goes back to the fermenter passing through conduit 7. Fermenter 1 receives, at regular intervals, an amount of nutrient mixture, coming from tank 6, necessary to make up for the amount of permeated substance that is conveyed from the ultrafiltration unit to receiver 8.

As the phosphorylation of glucose to FDP is the result of the combined action of exoquinase and phosphofructoquinase, which require the presence of ATP to carry on their effects, it is necessary, in order that the process be continuously carried out, to maintain a minimum pre-determined level of both ATP and NAD (nicotinamide adenine dinucleotide) (the latter co-factor being indispensable for regenerating ATP by means of the alcoholic fermentation cycle that necessarily accompanies the enzymatic production of FDP by means of yeast).

As both these factors, because of their low molecular weight, permeate the hollow fibers of unit 3, in order to make up for the leakage thereof an amount equal to 2% v/v deproteinized yeast extract is added to the nutrient mixture. The fructose-1,6-diphosphate present in the permeated substance collected in receiver 8 can be recovered by feeding such permeated substance to an anionic resin column, e.g. by the process described in the Patent Application No. 24355 A/83 of the same Applicant. This application corresponds to U.S. Pat. No. 4,575,549.

The invention will be now described in detail, through the following merely indicative, non-limiting examples.

The described plant for the continuous manufacture of FDP can even work by a discontinuous operation, whereby the phosphorylation of glucose to FDP takes place in batch at regular intervals, by adding the necessary amount of nutrient mixture at each cycle, and by recovering FDP from the yeast suspension at the end of each cycle, by means of ultrafiltration.

EXAMPLE 1

50 g centrifuged yeast, coming from the DREHER ale house of Popoli, is permeabilized and then immobilized by glutaraldehyde, according to the process described in the Italian Patent Application No. 19865 A/86 which is detailed on page 4 of the specification.

To the yeast (re-suspended in 30 ml tap water) there is added 2 ml of a 20% magnesium chloride solution, as well as 20 ml nutrient mixture (2M dextrose, 1M sodium phosphate and phosphoric acid until pH 6.5). The yeast is double boiler heated at 35° C. for 1 hour. There is added 50 ml disintegrated yeast, 30 mg dithiothreitol and, after cooling the mass to 28° C., 1.5 ml 25% glutaraldehyde. After 60' the mass is centrifuged at 3000 r.p.m. for 15', the supernatant is removed, the "pellet" is re-suspended in water (30% w/v) and fed to a 250 ml volume reactor connected with a hollow fiber ultrafiltration unit with overall membrane surface of 300 cm$^2$ and nominal porosity of 0.1$\mu$. After adding 40 ml nutrient mixture and regulating the thermostat to 28° C., the suspension is re-circulated through the unit at a 900 ml/min. flow rate.

After a preliminary 5 hours phase wherein the adjustment valve of the concentrate is wide open (with actually no permeation), the maximum FDP (14 mg/ml) concentration is reached in the reactor. Then, by partly preventing the return flow of the concentrate, the outflow rate of the permeated substance is set to 20 ml/h, the reactor being contemporarily fed at the same flow rate with diluted nutrient mixture (1:3) to which was added 2% deproteinized yeast extract.

Under these conditions the concentration of FDP in the permeated substance is practically constant over a week. This corresponds to an output of 134 mg FDP/g wet yeast per day.

EXAMPLE 2

50 g centrifuged yeast coming from the PERONI ale house of Bari is permeabilized and then immobilized by glutaraldehyde in the way described in Example 1.

The phosphorylation of glucose to FDP is carried out in the same reactor/ultrafiltration unit system of Example 1.

There is added 50 ml nutrient mixture, 10 ml deproteinized yeast extract and the temperature is set to 28° C. After 10 hours, over which time the maximum FDP concentration (58–60 mg/ml) is generally reached, the yeast suspension is ultrafiltered to recover the produced FDP.

This is achieved by re-circulating the suspension at a flow rate of 1.500 ml/min. and by adjusting the aperture of the control valve of the concentrate, so as to have inside the unit a working pressure of 15 psi. Under these conditions an average permeation flow of 5 ml/min. is obtained.

In order to avoid that the fibers be clogged as the yeast concentration continually increases, during the ultrafiltration step 50 ml diluted nutrient mixture 1:8 is added to the reactor per each 50 ml of the collected permeated substance. 250 ml overall permeated substance is collected at an average FDP concentration of 25–28 mg/ml.

Then another cycle is started, comprising adding another 50 ml deproteinized yeast extract, incubating at 28° C. for 10 h, ultrafiltering etc.

The FDP output is practically constant, in these circumstances, for 8–10 days, with an average output of 250 mg FDP/g wet yeast per day, during a non-stop overnight working.

An expert in the art can provide many changes and variations, that should all fall, however, within the ambit of the present invention.

We claim:

1. A process for the continuous production of fructose-1,6-diphosphate, which comprises phosphorylating dextrose by means of glutaraldehyde-treated yeast continuously supplied with a nutrient mixture and continuously recovering fructose-1,6-diphosphate by permeation across a hollow fiber ultrafiltration unit.

2. A process according to claim 1, wherein a suspension of glutaraldehyde-treated yeast, to which was added a nutrient mixture of dextrose and phosphates, is continuously re-circulated through a hollow fiber ultrafiltration unit.

3. A process according to claim 1 wherein the employed yeast is either *Saccharomyces carlsbergensis* or *Saccharomyces cerevisiae*.

4. A process according to claim 1, wherein said glutaraldehyde-treated yeast is present as a concentration of 20–35% (wet weight/volume) and wherein the nutrient mixture consists of dextrose 1M, sodium phosphate 0.5M and phosphoric acid until pH 6.5.

5. A process according to claim 1, comprising providing an addition of 2% v/v deproteinized yeast extract to the nutrient mixture, in order to guarantee the presence of the necessary minimum amount of ATP and NAD, which serve for phosphorylating glucose to FDP.

6. A process according to claim 1, for continuous production of fructose-1,6-diphosphate wherein yeast is continuously recirculated through the ultrafiltration unit, at high permeation speed.

7. A process according to claim 1 wherein the recovery of FDP is effected at a pressure of 12–15 psi and at a permeation speed of 1 ml/h/cm$^2$, by adding to the yeast suspension in the bioreactor 50 ml diluted nutrient mixture (1:8) per each 50 ml of collected permeated substance.

* * * * *

UNITED STATES PATENT AND TRADEMARK OFFICE
CERTIFICATE OF CORRECTION

PATENT NO. : 4,920,049

DATED : April 24, 1990

INVENTOR(S) : Guillermo M. Bisso

It is certified that error appears in the above-identified patent and that said Letters Patent is hereby corrected as shown below:

On the title page:
    [75] Inventors: change "Guglielmo M. Bisso" to
  -- Guillermo M. Bisso --

Signed and Sealed this

Fifth Day of May, 1992

Attest:

DOUGLAS B. COMER

*Attesting Officer*     *Acting Commissioner of Patents and Trademarks*